United States Patent [19]

Sugiyama et al.

[11] 4,089,964
[45] May 16, 1978

[54] METHOD OF CONTROLLING FUNGAL DISEASES IN PLANTS AND COMPOSITIONS EFFECTIVE THEREFOR

[75] Inventors: Hironari Sugiyama; Isao Chiyomaru; Itsuki Okuda, all of Shimizu; Hisaaki Yamamoto, Funabashi; Hideo Ito, Onomichi, all of Japan

[73] Assignee: Kumiai Chemical Industry Co., Ltd., Tokyo, Japan

[21] Appl. No.: 782,267

[22] Filed: Mar. 28, 1977

Related U.S. Application Data

[63] Continuation-in-part of Ser. No. 864,224, Oct. 6, 1969, Pat. No. 4,059,635.

[51] Int. Cl.² .................... A01N 9/12; A01N 9/14; A01N 9/22
[52] U.S. Cl. .................... 424/270; 424/337
[58] Field of Search .................... 424/270, 337

[56] References Cited

U.S. PATENT DOCUMENTS

| 3,138,519 | 6/1964 | Riden, Jr. et al. | 424/337 |
| 3,442,955 | 5/1969 | Newallis | 424/337 X |

FOREIGN PATENT DOCUMENTS

| 871,679 | 5/1971 | Canada. |
| 1,079,379 | 3/1954 | Germany. |
| 4,743,933 | 11/1972 | Japan. |
| 483,368 | 1/1973 | Japan. |

*Primary Examiner*—Allen J. Robinson
*Attorney, Agent, or Firm*—I. Walton Bader

[57] ABSTRACT

Method of controlling fungal diseases in plants and compositions effective therefor are shown. The method comprises the steps of applying an effective amount of a substituted derivative of 1,1,-dichloroalkene-1 of the general formula

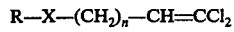

$$R-X-(CH_2)_n-CH=CCl_2$$

In this generalized formula R is an alkyl group having 1 to 12 carbon atoms, a phenyl group, a di-chloro-phenyl group, a methyl-phenyl group, a nitro-phenyl group, a benzyl group, a chloro-benzyl group, a di-chloro-benzyl group, a methyl-benzyl group, a phenethyl group or a benzothiazolyl group; X is sulfur, a sulfinyl group or a sulfonyl group; and $n$ is an integer of 3,5, and 7.

3 Claims, No Drawings

METHOD OF CONTROLLING FUNGAL DISEASES IN PLANTS AND COMPOSITIONS EFFECTIVE THEREFOR

This application is a continuation-in-part of our co-pending application Ser. No. 864,224 filed Oct. 6, 1969, now U.S. Pat. No. 4,059,635, issued 11-22-77.

DISCUSSION OF THE PRIOR ART

Various methods of controlling fungal diseases of plants appear in the literature. Chemical methods of controlling such diseases are also known. The use of the specific compound of this invention to control fungal diseases of plants, particularly rice plants, and, in particular, the diseases of rice blast (*Picicularia Oryzae*) does not appear to be shown heretofore. Of interest is the patent to Newallis, et. al., U.S. Pat. No. 3,442,955.

BRIEF DESCRIPTION OF THE INVENTION

The invention consists of a Method of controlling plant diseases, in particular Rice Blast (*Piricularia Oryzae*) by placing, on the infested plants, a powder, a spray, or similar method of mechanical application, of a compound having the generalized formula R—X—$(CH_2)_n$—CH=$CCl_2$ where R is selected from the group consisting of an alkyl group having from 1 to 12 carbon atoms, a phenyl group, a chloro-phenyl group, a di-chloro-phenyl group, a methyl-phenyl group, a nitro-phenyl group, a benzyl group, a chloro-benzyl group, a di-chloro-benzyl group, a methyl-benzyl group, a phenethyl group, and a benzothiazolyl group; X is selected from the group consisting of sulfur, a sulfinyl group and a sulfonyl group and $n$ is selected from integers 3,5, and 7.

DETAILED DESCRIPTION OF THE INVENTION

The present invention relates to new and useful substituted derivatives of 1,1-dichloroalkene-1 and their preparation and uses. The present invention further includes a method of controlling bacterial and fungal diseases of plants as well as a pesticidal and fungicidal composition containing the new derivatives of 1,1-dichloroalkene-1 as the active ingredient.

Among the bacterial and fungal diseases of rice plant, rice blast (*Piricularia oryzae*) gives the most severe damage to rice plant. In order to control the rice blast, various organic mercuric compounds such as phenyl mercuric acetate has widely been used in the rice field. When the organic mercuric compounds have been applied as fungicide in the rice field, it can be observed that a trade of mercuric compound remains in the hull of rice grains which are harvested therefrom. For health of people who like rice, it is now recommended to avoid the application of organic mercuric pesticide and instead thereof to employ any pesticidal compound containing no mercury for the control of rice blast when rice plant has came into ears.

Some organic phosphorus compounds and some polychlorinated phenyl compounds have been used in practice as the fungicide for the control of rice blast. Although certain compounds of them may have both the protection effect and the curative effect on the rice plants in the treatment of rice blast when tested in the laboratory, they can exhibit only either one of the protection effect and the curative effect when tested in the field. Among the known pesticidal compounds, there is no practical compound which is able to exhibit both the protection effect and the curative effect in combination for the treatment of rice blast when used in the rice field. In these circumstances, a demand is extensive and great to seek for such a mercury-free fungicide which is practically able to exhibit the protection effect and the curative or therapeutic effect in combination for the control of rice blast when used in the rice field.

We have now found that the new substituted derivatives of 1,1-dichloroalkene-1 of the general formula as stated below have antimicrobial activity and exhibit excellent combined protective and curative effects for the control of rice blast even when applied to in the rice field.

We have further found that, among the new substituted derivatives, the substituted phenylthio-1,1-dichloroalkene-1 is superior in protective fungicidal effect as well as in therapeutic effect to the unsubstituted phenylthio-1,1-dichloroalkene-1.

Moreover, some substituted derivative of 1,1-dichloroalkene-1 of the general formula as stated below can also be used as a fungicide for controlling sheath blight (*Pellicularia sasaki*), Bacterial leaf blight (*Xanthomonas oryzae*), Powdery mildew (*Sphaerotheca fuliginea*) and Anthracnose (*Colletotrichum lagenarium*).

Accordingly, the present invention provides new substituted derivatives of 1,1-dichloroalkene-1 of the general formula:

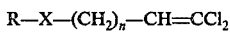

$$R-X-(CH_2)_n-CH=CCl_2$$

in which R is an alkyl group, preferably an alkyl group of 1 to 12 carbon atoms, a phenyl group, chlorophenyl group, dichloro-phenyl group, methyl-phenyl group, nitro-phenyl group, benzyl group, chloro-benzyl group, dichloro-benzyl group, methyl-benzyl group, phenetyl group or benzothiazolyl group; X is a sulfur atom, sulfinyl group or sulfonyl group; and $n$ is an integer of 3,5 or 7.

The new derivatives of 1,1-dichloroalkene-1 of the present invention include the following specific compounds as identified in Table 1 below.

Table 1

| Compounds | Compound No. | Remarks |
|---|---|---|
| 5-Methylthio-1,1-dichloropentene-1 | 1 | Clear, colorless liquid of b.p. of 102–108° C/0.15 mmHg, Refractive index $(n_D^{20})=1.5148$ |
| 7-Methylthio-1,1-dichloroheptene-1 | 2 | Clear, colorless liquid of b.p. of 136–145° C at 22 mmHg, $(n_D^{20})=1.5070$ |
| 5-Isopropylthio-1,1-dichloropentene-1 | 3 | Clear, yellow colored liquid of b.p. of 75–82° C/0.15 mmHg, $(n_D^{20})=1.5020$ |
| 9-Isopropylthio-1,1-dichlorononene-1 | 4 | Clear, yellow colored liquid of b.p. of 115–123° C/0.3 mmHg, $(n_D^{20})=1.4938$ |
| 7-Butylthio-1,1-dichloroheptene-1 | 5 | Liquid of b.p. of 103–109° C at 0.1 mmHg, $(n_D^{20})=1.4979$ |
| 7-Dodecylthio-1,1-dichloroheptene-1 | 6 | Liquid of b.p. of 172–179° C. at 0.01 mmHg, $(n_D)=1.4880$ |
| 5-Phenylthio-1,1-dichloropentene-1 | 7 | Liquid of b.p. of 114–120° C. at 0.2 mmHg, $(n_D^{20})=1.5779$ |
| 7-Phenylthio-1,1-dichloroheptene-1 | 8 | Liquid of b.p. of 124–130° C. at 0.01 mmHg, $(n_D^{20})=1.5620$ |
| 5-(Para-chlorophenyl-thio)-1,1-dichloro- | 9 | Liquid of b.p. of 125–132° C. at |

Table 1-continued

| Compounds | Compound No. | Remarks |
|---|---|---|
| pentene-1 | | 0.006 mmHg, $(n_D^{26.5}) = 1.5840$ |
| 7-(Para-chlorophenylthio)-1,1-dichloroheptene-1 | 10 | Clear, yellow colored liquid of b.p. of 135° C. to 140° C. at 0.008 mmHg, $(n_D^{22}) = 1.5781$ |
| 9-(Para-chlorophenylthio)-1,1-dichlorononene-1 | 11 | Clear, brown colored liquid of b.p. of more than 160° C/0.01 mmHg, $(n_D^{20}) = 1.5185$ |
| 7-(2',5'-dichlorophenylthio)-1,1-dichloroheptene-1 | 12 | Liquid of b.p. of 163° C. at 0.008 mmHg, $(n_D^{20}) = 1.5860$ |
| 5-(Para-methylphenylthio)-1,1-dichloropentene-1 | 13 | Clear, yellow colored liquid of b.p. of 118–121° C/0.005 mmHg, $(n_D^{20}) = 1.5718$ |
| 7-(Para-methylphenylthio)-1,1-dichloroheptene-1 | 14 | Clear, yellow colored liquid of b.p. of 137–143° C. at 0.01 mmHg, $(n_D^{20}) = 1.5587$ |
| 9-(Para-methylphenylthio)-1,1-dichlorononene-1 | 15 | Clear, yellow colored liquid of b.p. of more than 100° C at 0.01 mmHg, $(n_D^{20}) = 1.5486$ |
| 5-(Para-nitrophenylthio)-1,1-dichloropentene-1 | 16 | Liquid of b.p. of more than 150° C. at 0.007 mmHg, |
| 7-(Para-nitrophenylthio)-1,1-dichloroheptene-1 | 17 | Liquid of b.p. of more than 150° C. at 0.01 mmHg |
| 5-Benzylthio-1,1-dichloropentene-1 | 18 | Clear, yellow colored liquid of b.p. of 115–125° C./0.01 mmHg, $(n_D^{20}) = 1.5652$ |
| 7-Benzylthio-1,1-dichloroheptene-1 | 19 | Liquid of b.p. of 145–147° C./0.03 mmHg, $(n_D^{29}) = 1.5529$ |
| 9-Benzylthio-1,1-dichlorononene-1 | 20 | Clear, faint yellow colored liquid of b.p. of 143–147° C. at 0.003 mmHg, $(n_D^{20}) = 1.5437$ |
| 5-(Para-chlorobenzylthio)-1,1-dichloropentene-1 | 21 | Liquid of b.p. of 141–144° C. at 0.015 mmHg $(n_D^{20}) = 1.5749$ |
| 7-(Para-chlorobenzylthio)-1,1-dichloroheptene-1 | 22 | Liquid of b.p. of 150–160° C./0.007 mmHg, $(n_D^{20}) = 1.5629$ |
| 7-(2',4'-dichlorobenzylthio)-1,1-dichloroheptene-1 | 23 | Liquid of b.p. of 170–175° C./0.01 mmHg, $(n_D^{20}) = 1.5638$ |
| 5-(Para-methylbenzylthio)-1,1-dichloropentene-1 | 24 | Liquid of b.p. of 118–121° C. at 0.005 mmHg, $(n_D^{20}) = 1.5718$ |
| 7-(Para-methylbenzylthio)-1,1-dichloroheptene-1 | 25 | Liquid of b.p. of 137–143° C. at 0.01 mmHg, $(n_D^{20}) = 1.5587$ |
| 5-Phenetylthio-1,1-dichloropentene-1 | 26 | Liquid of b.p. of 127–130° C. at 0.003 mmHg, $(n_D^{20}) = 1.5596$ |
| 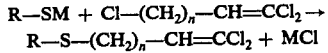 | | |
| 7-Phenetylthio-1,1-dichloroheptene-1 | 27 | Liquid of b.p. of 142–150° C. at 0.005 mmHg, $(n_D^{20}) = 1.5552$ |
| 5-[benzothiazolyl-(2)-thio]-1,1-dichloropentene-1 | 28 | Clear, brown colored liquid of b.p. of 160° C./0.02 mmHg, $(n_D^{36.5}) = 1.6387$ |
| 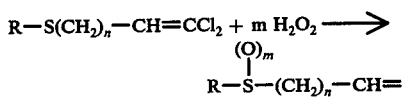 | | |
| 7-[Benzothiazolyl-(2)-thio]-1,1-dichloroheptene-1- | 29 | Red colored liquid of b.p. of more than 140° C. at 0.1 mmHg, $(n_D^{20}) = 1.6102$ |
| 9-[Benzothiazolyl-(2)-thio]-1,1-dichlorononene-1 | 30 | Clear, brown colored liquid of b.p. of more than 145° C. at 0.01 mmHg, $(n_D^{20}) = 1.5579$ |
| 7-Methylsulfinyl-1,1-dichloroheptene-1 | 31 | Clear, colorless liquid of b.p. of 133–138° C. at 0.2 mmHg, $(n_D^{20}) = 1.5167$ |
| 7-(Para-chlorobenzylsulfinyl)-1,1-dichloroheptene-1 | 32 | Liquid of b.p. of more than 180° C. at 0.01 mmHg, $(n_D^{20}) = 1.5752$ |
| 7-Phenylsulfonyl-1,1-dichloroheptene-1 | 33 | Liquid of b.p. of 150–160° C./0.02 mmHg, $(n_D^{24}) = 1.5393$ |
| 7-(para-chlorophenylsulfonyl)-1,1-dichloroheptene-1 | 34 | Clear, yellow colored liquid of b.p. of 180–190° C. at 0.01 to 0.02 mmHg, $(n_D^{29}) = 1.5508$ |
| 7-(2',5'-dichlorophenyl-sulfonyl)-1,1-dichloropeptene-1 | 35 | Liquid of b.p. of more than 150° C. at 0.08 mmHg, $(n_D^{20}) = 1.5790$ |

The new substituted derivatives of 1,1-dichloroalkene-1 of the present invention may be prepared in various ways.

A most convenient way to prepare them is to react a mercaptide of the formula R-SM with a trichloroalkene-1 of the formula $Cl-(CH_2)_n-CH=CCl_2$ in a suitable organic solvent such as ethanol in which the reagents are soluble. The reaction proceeds according to the following equation:

$$R-SM + Cl-(CH_2)_n-CH=CCl_2 \rightarrow$$
$$R-S-(CH_2)_n-CH=CCl_2 + MCl$$

wherein R and $n$ have the same meanings as defined hereinbefore; and M is an alkali metal atom or ammonium group. In this reaction, as the starting mercaptide, there may be used those which correspond to the following mercaptans:- methyl mercaptan, ethyl mercaptan, isopropyl mercaptan, butyl mercaptan, dodecyl mercaptan, phenyl mercaptan, 2-chlorophenyl mercaptan, 4-chlorophenyl mercaptan, 4-nitrophenyl mercaptan, 2,4-dichlorophenyl mercaptan, 2,5-dichlorophenyl mercaptan, 3,4-dichlorophenyl mercaptan, 4-methylphenyl mercaptan, benzyl mercaptan, 4-chlorobenzyl mercaptan, 4-methylbenzyl mercaptan, phenetyl mercaptan, benzothiazolyl mercaptan and the like. The mercaptide may be formed in situ in the reaction medium by reacting the corresponding mercaptans with an alkali metal. The starting material $Cl-(CH_2)_n-CH=CCl_2$ may be prepared by telomerization of ethylenically unsaturated aliphatic hydrocarbons such as ethylene with carbon tetrachloride, followed by the dehydrochlorination.

A further way to prepare the new derivatives of 1,1-dichloroalkene-1 of the present invention is to oxidise the products of the above-mentioned reaction with hydrogen peroxide or organic per-acid such as perbenzoic acid or peracetic acid. In this case, the reaction may be represented by the following equation:

$$R-S(CH_2)_n-CH=CCl_2 + m\,H_2O_2 \longrightarrow$$
$$R-\overset{(O)_m}{\underset{|}{S}}-(CH_2)_n-CH=CCl_2 + m\,H_2O$$

wherein R and $n$ have the same meanings as defined above, and $m$ is an integer of 1 or 2.

According to the present invention, therefore, there is provided a process for the preparation of the new substituted derivatives of 1,1-dichloroalkene-1 of the general formula:

$$R-X-(CH_2)_n-CH=CCl_2$$

in which R is an alkyl group, a phenyl group, chlorophenyl group, dichlorophenyl group, methylphenyl group, nitrophenyl group, benzyl group, methylbenzyl group, chlorobenzyl group, dichlorobenzyl group, phenetyl group or benzothiazolyl group; and X is a sulfur atom or a sulfinyl group or sulfonyl group; and $n$ is an integer of 3,5 or 7, characterised in that a mercaptide of the formula:

$$R-SM$$

in which R has the same meanings as state above and M is an alkali metal atom or ammonium group is reacted with a trichloroalkene-1 of the formula:

$$Cl-(CH_2)_n-CH=CCl_2$$

in which $n$ is 3,5 or 7, in the presence of an organic solvent in which the reagents are soluble, and that the substituted 1,1-dichloroalkene-1 derivatives so obtained is oxidised, if desired.

As mentioned previously, the new substituted derivatives of 1,1-dichloroalkene-1 of the present invention have antimicrobial activity, and particularly fungicidal activity to *Piricularia oryzae*, and they are useful for the protection of plants from attack by phyto-pathogenic micro-organisms as well as for the therapeutic treatment of plants which have been infected by phyto-pathogenic micro-organisms.

According to the present invention, therefore, there is also provided a method of controlling fungal diseases of plants which comprises applying to plants an effective amount of at least one of the new substituted derivatives of 1,1-dichloroalkene-1 of the general formula as stated hereinbefore.

In particular, the present invention provides a method of controlling the rice blast which comprises applying to rice plant an effective amount of at least one of the new substituted derivatives of 1,1-dichloroalkene-1 of the general formula as stated hereinbefore.

For use in the control of fungal diseases, the new substituted derivatives of 1,1-dichloroalkene-1 of the present invention may be applied to plants, in admixture with an inert carrier which may be either solid or liquid.

Accordingly, the present invention further provides a fungicidal composition which contains as the active ingredient at least one of the new substituted derivatives of 1,1-dichloroalkene-1 of the general formula as stated hereinbefore, in admixture with a carrier which is inert to the active ingredient compound.

The fungicidal composition of the present invention may be formulated in the form of dust, wettable powder, solution, suspension or emulsion, as desired. Solid carrier may be, for example, diatomaceous earth, talc, kaolin, clay, and the like. Liquid carrier may be, for example, water and organic solvents such as xylene, toluene, benzene, methanol, ethanol, acetone, cyclohexanone, dimethylformamide and the like. The fungicidal composition of the present invention further may contain a variety of surface-active agents as emulsifying agent, spreading agent, dispersing agent and/or wetting agent etc.

The proportion of the active ingredient in the composition of the present invention may vary in a wide range but preferably in a range of 1% to 50% by weight. The composition of the present invention may be dispersed or diluted in water for spraying.

When a composition of the present invention is prepared in the form of an emulsifiable solution, it may be recommended that one or more emulsifying agents such as polyoxyethylene alkylaryl ethers, polyoxyethylene alkyl ethers, polyoxyethylene aliphatic acid esters, alkylaryl sulfonates and polyoxyethylene polyalkyldiphenyl ethers or a mixture of two or more of them is or are incorporated at an amount of 5 to 15% by weight into a solution of the active ingredient compound dissolved in an organic solvent such as xylene, toluene, or mixed organic solvents.

When the composition of the present invention is formulated as wettable powder, it is then recommendable that 1 to 3% by weight of a wetting agent such as alkylaryl sulfonates, polyoxyethylene alkylaryl ether lauryl sulfate and polyoxyethylene alkylaryl sulfonates, as well as 1 to 3% by weight of a dispersing agent such as lignin sulfonate, polyvinyl alcohol, carboxymethyl cellulose, methyl cellulose, alkylaryl sulfonate-formaldehyde condensate are incorporated in a powdered mixture of the active ingredient compound with a suitable solid carrier such as talc.

If desired, the composition of the present invention may further contain varying amounts of another pesticide, fungicide such as ferric methane-arsonate, pesticide such as sevin (registered trade name), "Sumithione" (registered trade name) and BHC etc.

The invention is now illustrated with reference to the following Examples, but to which the present invention is not limited.

EXAMPLE 1

To a solution of 23 g. (0.1 mol) of metallic sodium in 150 ml. of ethyl alcohol was added 14.4 g. (0.1 mol) of benzyl mercaptan, and the mixture was heated for 1 hour under agitation. To the mixture was then added 23 g. (0.1 mol) of 1,1,9-trichlorononene-1, and the admixture was agitated at about 80° C. for 8 hours. After the completed reaction, the reaction mixture was poured into a large quantity of water. An oil deposited, which was then extracted with benzene. The extract was dried with anhydrous sodium sulfate and distilled to evaporate the benzene. The concentrated residue was purified by fractional distillation under vacuum. 25.0 g. of 9-benzylthio-1, 1-dichlorononene-1 of the formula:

$$C_6H_5-CH_2-S-(CH_2)_7-CH=CCl_2$$

was obtained as a clear, faint yellow colored liquid having boiling point of 143°–147° C. at 0.003 mmHg.

Yield: 79% on the basis of the theoretical value.

EXAMPLE 2

The procedure of Example 1 was repeated using methyl mercaptan and 1,1,5-trichloropentene-1. 5-Methylthio-1,1-dichloropentene-1 of the formula $CH_3-S-(CH_2)_3CH=CCl_2$ was obtained as a clear and colorless liquid which boiled at 102°–103° C. at 0.15 mmHg.

EXAMPLE 3

The procedure of Example 1 was repeated using isopropyl mercaptan and 1,1,5-trichloropentene-1. 5-Isopropylthio-1,1-dichloropentene-1 of the formula

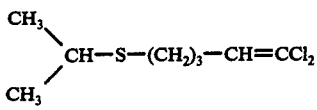

was obtained as clear and yellow colored liquid which boiled at 75°–82° C. at 0.15 mmHg.

EXAMPLE 4

To a solution of 2.3 g. of sodium in 150 ml. of ethanol was added 124 g. (0.1 mol) of para-mehylphenyl mercaptan, and the mixture was heated for 30 minutes under agitation. 20.2 g. (0.1 mol) of 1,1,7-trichloroheptene-1 was then added thereto, and the mixture was agitated at about 80° C. for 8 hours. After the completed reaction, the reaction mixture was poured into water. The oily material deposited was extracted with benzene. The organic layer was dried with anhydrous sodium sulfate and concentrated by evaporating the benzene. When the residue was distilled under vacuum, 7-(para-methylphenylthio)-1,1-dichloroheptene-1 of the formula

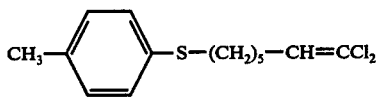

was obtained as a clear and yellow colored liquid which boiled at 137° – 143° C. at 0.01 mmHg. Yield was 25.6 g. (88.5%).

EXAMPLE 5

The procedure of Example 4 was repeated using 0.1 mol. of benzothiazolyl mercaptan and 0.1 mol. of 1,1,7-trichloroheptene-1. At a yield of 81%, 7-[benzothiazolyl-(2)-thio]-1,1-dichloroheptene-1 was obtained as red colored liquid which boiled above 140° C. at 0.1 mmHg.

EXAMPLE 6

Fifty g. of an aqueous solution containing 20% of sodium methylmercaptide was dissolved in 150 ml. of dimethylformamide, and 28.8 g. of 1,1,7-trichloroheptene-1 was added thereto at room temperature together with a catalytic amount of potassium iodide. The mixture was heated at 80° – 90° C. for 10 hours under agitation. After the completed reaction, the reaction mixture was cooled to room temperature and then poured into about 1.5 l. of water. The oily material deposited was extracted with benzene. The organic layer was dried with anhydrous sodium sulfate and concentrated by evaporating the solvent. When the residue was distilled under vacuum, 28 g. of 7-methylthio-1,1-dichloroheptene-1 was obtained as clear and colorless liquid which boiled at 136° – 145° C. at 22 mmHg.

EXAMPLE 7

Twenty g. of an aqueous solution of 30% hydrogen peroxide was added to a solution of 21.3 g. of 7-methylthio-1,1-dichloroheptene-1 in 150 ml. of glacial acetic acid under agitation while the reaction temperature was kept at about 15° C. by cooling the reaction mixture with ice-water. The mixture was further stirred for 1 hour at 15° C. After the completed reaction, the reaction mixture was poured into about 2 l. of water and the oily material deposited was extracted with benzene. The organic layer was dried with anhydrous sodium sulfate and then concentrated by evaporating the solvent. When the residue was distilled under vacuum, 17.2 g. of 7-methylsulfinyl-1,1-dichloroheptene-1 was obtained as clear and colorless liquid which boiled at 133° – 138° C. at 0.2 mmHg.

EXAMPLE 8

To a solution of 28.9 g. (0.2 mol) of parachlorophenyl mercaptan in 50 ml. of benzene was added dropwise 11.5 g. of a sodium dispersion containing 40% metallic sodium which corresponded to 0.2 mol of sodium. After the addition was complete, the mixture was heated for 2 hours under reflux. 100 ml. of dimethylformamide and 40.3 g. (0.2 mol) of 1,1,7-trichloroheptene-1 were added thereto, and the mixture was further heated for 15 hours under reflux. After the completed reaction, the reaction mixture was washed with water. The remaining benzene solution was then dried with anhydrous sodium sulfate and concentrated by distilling off the solvent. When the residue was distilled under vacuum, 35 g. of 7-(para-chlorophenylthio)-1,1-dichloroheptene-1 was collected as a fraction which boiled at 135° – 140° C. at 0.008 mmHg. This product was a clear and yellow colored liquid.

EXAMPLE 9

To a solution of 20 g. of para-chlorobenzene sulfinic acid sodium salt in 200 ml. of dimethylformamide was added dropwise 20 g. of 1,1,7-trichloroheptene-1 under agitation. When the addition had been completed, the mixture was heated at 80° to 90° C. for 10 hours. After the completed reaction, the reaction mixture was poured into 1 l. of water. The organic layer separated was extracted with benzene and the extract was dried with anhydrous sodium sulfate. When the residue was distilled under vacuum, 16 g. of 7-(para-chlorophenylsulfonyl)-1,1-dichloroheptene-1 was collected as a fraction which boiled at 180° – 190° C. at 0.01 – 0.02 mmHg. This product was a clear and yellow colored liquid. Infra-red absorption spectrum of this product showed the absorption band at 1150 cm$^{-1}$ due to the presence of the sulfonyl group.

EXAMPLE 10

Five Parts (by weight) of the compound No. 1, that is, 5-methyl-1,1-dichloropentene-1, 45 parts of talc, 47 parts of clay and 3 parts of white carbon were mixed together and ground in a mill. The powder may be applied to plants in the form of dust.

EXAMPLE 11

Five Parts (by weight) of the compound No. 16, this is, 5-(para-nitro-phenylthio)-1,1-dichloropentene-1, 45 parts of talc, 47 parts of clay and 3 parts of white carbon were mixed together and ground in a mill. The resulting powder may be suitable for dusting.

EXAMPLE 12

Twenty five Parts (by weight) of the compound No. 15, that is, 9-(para-methyl-phenylthio)-1,1-dichlorononene-1, 30 parts of diatomaceous earth, 10 parts of white carbon, 30 parts of clay and 5 parts of a wetting agent (a mixture of polyalkylaryl polyglycol ethers) were mixed together and ground. The wettable powder so obtained may easily be diluted in water and the resulting suspension may be suitable for spraying.

EXAMPLE 13

Twenty five Parts of the compound No. 16, that is, 5-(para-nitrophenylthio)-1,1-dichloropentene-1, 30 parts of diatomaceous earth, 10 parts of white carbon, 30 parts of clay, and 5 parts of a wetting agent (a mixture of alkylaryl polyglycol ethers) were mixed together and ground. The wettable powder so obtained may readily diluted with water and the resulting suspension may be suitable for spraying.

EXAMPLE 14

Fifty Parts of the compound No. 13, that is, 5-(Para-methylphenylthio)-1,1-dichloropentene-1, 35 parts of xylene and 15 parts of an emulsifying agent (a mixture of alkylaryl polyglycol ethers and alkylaryl sulfonates) were mixed together and agitated to prepare a uniform solution. This emulsifiable solution may readily be converted into an emulsion suitable for spraying, when diluted with water.

EXAMPLE 15

Fifty Parts of the compound No. 18, that is, 5-benzylthio-1,1-dichloropentene-1, 35 parts of xylene and 15 parts of an emulsifying agent (a mixture of alkylaryl polyglycol ethers and alkylaryl sulfonates) were mixed together and agitated enough to give a uniform solution. The resulting emulsifiable solution may readily be converted into an emulsion suitable for spraying, when diluted with water.

EXAMPLE 16

This Example illustrates the tests of controlling rice blast by treatment with the new substituted derivatives of 1,1-dichloroalkene-1 of this invention.

The therapeutic effect test and the protective effect test were made with respect to 4-leaf stage paddy field rice plant (*Variety*, Aichi Asahi) planted in a pot of 15 cm diameter, respectively.

An emulsifiable concentrate as prepared according to Example 4, which contains an active compound as shown in the following Table 2, was diluted with water to a concentration of 500 ppm of the active compound and the thus diluted solution was sprayed in an amount of 30 cc per pot.

In the therapeutic effect test, the rice plants grown in pots were inoculated with aqueous suspension of spores of *Piricularia oryzae* and the diluted solution of chemicals was sprayed on infested plants on the 3rd day after inoculation. The effectiveness was assessed on the 7th day after inoculation.

On the other hand, in the protective effect test, the diluted solution was prayed on the 3rd day before the inoculation. The effectiveness was assessed on the 7th day after inoculation.

The controlling value was calculated according to the following equation.

$$\text{Controlling valve (\%)} = 100 - \left(\frac{\text{disease degree in sprayed plants}}{\text{disease degree in non-sprayed plants}}\right) \times 100$$

In the therapeutic effect test, the term "disease degree" in the above equation means a ratio of the number of actively diseased spots to the total number of actively and inactively diseased spots. In the protective effect test, the "disease degree" merely means the number of diseased spots.

Table 2

| Active compound tested | Experiment result (therapeutic effect) | | |
|---|---|---|---|
| | | Concentration (ppm.) | Controlling value |
| Compound | 7 | 500 | 56 |
| | 10 | " | 95 |
| | 11 | " | 78 |
| | 13 | " | 75 |
| | 14 | " | 100 |
| | 15 | " | 79 |
| | 16 | " | 71 |
| | 17 | " | 73 |
| | 18 | " | 90 |
| | 19 | " | 99 |
| | 20 | " | 98 |
| | 21 | " | 97 |
| | 22 | " | 100 |
| | 23 | " | 91 |
| | 24 | " | 74 |
| | 25 | " | 92 |
| | 26 | " | 75 |
| | 27 | " | 99 |
| | 31 | " | 97 |
| | 32 | " | 71 |
| | 33 | " | 73 |
| | 34 | " | 72 |
| | 35 | " | 71 |

Table 3

| Active compound tested | Experiment result (Protective effect) | | |
|---|---|---|---|
| | | Concentration (ppm) | Controlling value |
| Compound | 1 | 500 | 77 |
| | 2 | " | 100 |
| | 3 | " | 75 |
| | 4 | " | 72 |
| | 5 | " | 71 |
| | 6 | " | 100 |
| | 7 | " | 53 |
| | 8 | " | 67 |
| | 9 | " | 100 |
| | 10 | " | 100 |
| | 11 | " | 100 |
| | 12 | " | 100 |
| | 13 | " | 100 |
| | 14 | " | 100 |
| | 15 | " | 100 |
| | 18 | " | 76 |
| | 19 | " | 100 |
| | 20 | " | 100 |
| | 21 | " | 92 |
| | 24 | " | 94 |
| | 25 | " | 100 |
| | 26 | " | 100 |
| | 27 | " | 100 |
| | 28 | " | 77 |
| | 29 | " | 100 |
| | 30 | " | 100 |
| | 31 | " | 100 |
| | 32 | " | 95 |
| | 33 | " | 100 |
| | 34 | " | 100 |
| | 35 | " | 93 |

The compound Nos. as indicated in Tables 2 & 3 are the same as shown in Table 1.

The foregoing description indicates how the objects of this invention are achieved.

We claim:

1. A method of controlling fungal diseases of rice plants which comprises applying to said plants a fungicidally effective amount of a composition containing an inert carrier and as the active ingredient a fungicidally effective amount of a compound having the formula R—X—(CH$_2$)$_n$—CH=CCl$_2$ wherein R is selected from the group consisting of alkyl having between one and twelve carbon atoms, phenyl, di-chlorophenyl, methylbenzyl, phenethyl and benzothiazolyl; X is selected from the group consisting of sulfur, sulfinyl and sulfonyl; and $n$ is an integer of 3,5 or 7.

2. A method of controlling fungal diseases as described in claim 1 wherein said fungal disease is rice blast, and said inert carrier is an emulsifying agent.

3. A method as described in claim 2 wherein said inert carrier consists of 10 parts of white carbon, 30 parts of clay, and 5 parts of a wetting agent, and 25 parts of said active ingredient.

* * * * *